US006489443B2

(12) United States Patent
Römisch et al.

(10) Patent No.: US 6,489,443 B2
(45) Date of Patent: Dec. 3, 2002

(54) PROCESS FOR THE PREPARATION OF A PROTEIN SOLUTION

(75) Inventors: Jürgen Römisch, Marburg (DE); Jörg Weisse, Ebsdorfergrund (DE); Jean Luc Veron, Sainte-Foy-les-Lyon (FR); Juliana Djordjevich, Chicago, IL (US); Wilfried Freudenberg, Cölbe (DE); Michel Grandgeorge, Marburg (DE); Barbara Kalina, Marburg (DE); Peter Kappus, Marburg (DE); Manfred Konrad, Vienna (AT); Gregory S. Rood, Winterville, NC (US); Werner Thill, Bourbonnais, IL (US)

(73) Assignee: Aventis Behring GmbH, Marburg (DE)

( * ) Notice: Subject to any disclaimer, the term of this patent is extended or adjusted under 35 U.S.C. 154(b) by 9 days.

(21) Appl. No.: 09/350,120

(22) Filed: Jul. 9, 1999

(65) Prior Publication Data

US 2002/0035062 A1 Mar. 21, 2002

(30) Foreign Application Priority Data

Jul. 10, 1998 (DE) .......................... 198 30 914

(51) Int. Cl.$^7$ ............................ C07K 1/00; C07K 2/00; A61K 38/00
(52) U.S. Cl. ...................... 530/350; 530/362; 530/363; 530/364; 514/2
(58) Field of Search ................... 530/362, 363, 530/364, 350; 514/2

(56) References Cited

U.S. PATENT DOCUMENTS 6,022,954 A * 2/2000 Dernis et al. ............... 530/364

OTHER PUBLICATIONS

Burden et al. Biotechnology: Proteins to PCR, A Course in Strategies and Lab Techniques, Birkhauser, Boston, 6–10 and 55–75, 1995.*
Machu et al. Selective Actions of a Detergent on Ligand–Gated Ion Channels Expressed in Xenopus Oocytes, J. Pharmacol. Exp. Ther. 284(1): 32–36, Jan. 1998.*

* cited by examiner

Primary Examiner—Karen Cochrane Carlson
Assistant Examiner—Holly Schnizer
(74) Attorney, Agent, or Firm—Finnegan, Henderson, Farabow, Garrett and Dunner, L.L.P.

(57) ABSTRACT

A process for the preparation of a protein solution is described which is not prone to flock or particle formation even on heat treatment, the heat treatment being carried out in a glass vessel which has been rinsed out beforehand with a detergent solution and then with distilled water or another detergent-free solvent.

6 Claims, No Drawings

PROCESS FOR THE PREPARATION OF A PROTEIN SOLUTION

The invention provides a process for the preparation of a protein solution which is not prone to floc or particle formation even on heat treatment.

It is known that particles or flocs are frequently formed in protein-containing solutions. In particular in the case of preparations which are administered parenterally to the patient, floc or particle formation poses a serious problem. These particles have to be removed prior to administration using a filter specifically provided for this purpose or, if this is not possible, the preparation has to be discarded. The causes of such a particle formation are often unclear, but this problem is observed in particular on heat treatment of protein solutions. This can be illustrated using albumin as an example:

For a long time, albumin, which is prepared from human plasma by purification, has been administered to patients in emergencies for substituting the blood volume. The albumin is usually obtained from human plasma by fractional alcohol precipitations in the cold, by which the other plasma components are separated off. For medicinal use, it is customary to employ albumin solutions which contain this protein in amounts of 5, 20 or 25%. To eliminate the risk of an infection of the patients by bacteria or viruses which may be present in a contaminated albumin solution, the albumin solution is as a rule subjected to a heat treatment in the final container. Here, in the presence of stabilizing additives, the albumin solution is pasteurized, for example by heating at approximately 60° C. for at least 10 hours.

During pasteurization, floc-like particles may form which, when the filled containers are gently shaken, become evident as opalescent and/or white conglomerates of greater or smaller size. Since parenteral administration of such particles has to be avoided, it is necessary to segregate and discard such filled containers. Filtration of a particle-containing solution prior to administration is not practicable, since the filtration of the protein solution through a sterile filter is hindered by its relatively high viscosity.

Since the particles formed by protein aggregation are formed primarily during the pasteurization process and since it is not possible to remove them subsequently from the final filled container, it has already been attempted to reduce floc formation, or to prevent it entirely, by adding suitable agents. Thus, the European Patent 0 341 103 describes a process for stabilizing human albumin solutions in a container with the aid of a stabilizer where, in addition to the stabilizer, a surfactant, such as Tween® 80, Tween® 20, Pluronic® F68 or the laurate of polyethylene glycol 600 is added prior to the heat treatment. Here, above a certain detergent concentration, a considerably reduced number of flocs is observed, which is reduced even more, or completely prevented, when the detergent content is increased. However, it is a disadvantage that the detergent remains in the protein solution and is therefore administered to the patient together with the albumin. Although certain detergents are entirely suitable in certain concentration limits for administration since they can be tolerated and broken down in the organism, a preparation with as low a detergent content as possible, if any at all, is preferred and aimed for.

It was therefore the object to develop a process permitting the preparation of a protein solution which only contains very little detergent, if any at all, and which is not prone to floc or particle formation even on heat treatment.

It has now been found that such a protein solution can be prepared when the heat treatment is carried out in a glass vessel which has been rinsed out beforehand with a detergent solution and then with distilled water or another detergent-free solvent.

It is surprising that filling in a detergent-containing solution into the glass vessel intended for receiving the protein solution reduces or prevents the amount of flocs or particles formed on the subsequent heat treatment of the albumin solution which is then filled into this vessel, even though the vessel is rinsed with distilled water or another detergent-free solvent before the protein solution is filled in, so that only traces of detergent, if any at all, are still detectable in the pasteurized protein solution, but that nevertheless the proportion of particles is significantly reduced.

Suitable detergents are substances known to the person skilled in the art. Here, particular preference is given to nonionic detergents which are known under the trade names Tween®, Triton® and Pluronic®. The upper limit of the concentration of the detergent in the solution which is brought into contact with the glass vessel is defined solely by the solution in the liquid. However, the concentrations in solutions should not be less than 0.000001% by weight. The inner surface of the glass vessel should be wetted as completely as possible, and there is no limit to the duration of the incubation. The subsequent rinsing of the vessel with water or a detergent-free solution is intended to ensure the detergent in the ready-to-use protein solution is present only in traces, preferably in a concentration of less than 0.0002% by weight, or no longer detectable at all. This treatment of the glass vessel leads to the unexpected result that the proportion of particles in the filled-in protein solution after pasteurization is very low, as demonstrated by the example below.

The cause of the formation of flocs or particles in a protein solution during the heat treatment has hitherto not been understood completely, but the results of the present invention indicate that the inner surface of the vessel may be an important factor here. It is possible that the detergent prevents the formation of flocs by saturation of appropriate interaction sites which act as "particle nucleation centers". A particular advantage of the process according to the invention is the fact that only traces of detergent, if any at all, go into solution, and that the preparation is consequently only contaminated to a small extent, if it all.

Using the process according to the invention, it is possible to prevent floc or particle formation in various protein solutions. The process has proved to be very particularly successful for stabilizing albumin solutions and for solutions of blood clotting factors. The proteins can either be isolated from natural material, or they can be prepared by recombination or transgenically. The invention can be realized with all customary container glass types, in particular with those made from type I and type II glass.

It is not in every case that floc or particle formation in protein solution occurs only during heat treatment. Sometimes, a particle formation which can be prevented or reduced by the process according to the invention is observed even at room temperature or during prolonged storage. Quite generally, it can be said that the formation of protein oligomers, dimers or multimers induced by the surfaces of vessels can be reduced by the invention.

The process described above is illustrated in more detail using the particle formation of albumin during pasteurization as an example:

EXAMPLE:

Glass vessels (volume: 50 ml) were filled to the brim with a solution containing Tween® 80 in a concentration of 0.1% and incubated at room temperature for 30 minutes. The solution was removed by pouring out and the vessels were drained standing upside-down. They were then rinsed one to three times in water suitable for injection purposes (WFI). To this end, the vessels were again filled completely and then directly emptied again in a corresponding manner. The vessels were air-dried and then filled with a 20% strength albumin solution, and the vessels were closed with a stopper and subsequently incubated in a water bath at 60° C. for 10 hours. The vessels were placed in the water bath such that a high proportion of particles was induced. Vessels which had not been pretreated with detergent solutions served as controls. As positive controls, some of the albumin solution was admixed with Tween 80 and filled into untreated vessels. The amounts of detergent added were such that the end concentrations in the corresponding albumin solutions were between 0.0001% and 0.1%.

The number of particle-containing vessels was in each case determined by visual evaluation. The results (table) show that particles were registered in 60% of the control vessels (vessels which had not been pretreated with detergent). As expected, the filled containers serving as control (albumin solution with 0.1% of Tween) remained particle-free. With decreasing Tween 80 concentrations, the proportion of particles increased, and a considerable leap in this respect was observed between 0.0025% and 0.001% (see table). The vessels which had been pretreated with detergent-containing solution and then rinsed showed a significantly reduced proportion of flocs compared with the control, and only 5% of the vessels which had been rinsed once contained particles, and between 20 and 30% of the vessels which had been rinsed twice or three times.

The vessels were then opened, a sample was taken from each vessel and the Tween concentration was quantified. To this end, a modified test system according to Thoma et al. (Sci Pharm, 1964,3: 216–224) was employed.

Whereas in the controls (without Tween treatment), as expected, no detergent could be detected, approximately the theoretically expected concentrations were found in the solutions to which from 0.0001% to 0.1% of Tween had been added (with the exception of the contents outside the limits of the test).

In contrast, only traces, if any detergent at all, could be detected in the solutions which had been taken from the vessels which had been pretreated with a detergent and then rinsed. Even after rinsing the vessels only twice, the Tween 80 content of the albumin solutions was below the minimum detection limit of the test system.

Comparing the various experiments, it becomes evident that, at comparably reduced proportions of particles (i.e., for example, approximately 30%), only traces of Tween, if any, could be detected in the pretreated vessels (<0.0002%), but distinct amounts of detergent (0.002%) were found in the experiments with added Tween (the latter according to expectation). This means that, using the process that is claimed, the contamination of the albumin by detergents is reduced by a factor of at least 10, at the same reduction of the proportion of particles.

TABLE

| Experiments | Proportion of particles (%) (n = 10–25) | Conc. of Tween 80 (%) mean values from n = 3–8 |
|---|---|---|
| Control Samples/vessels without Tween 80 | 60 | <0.0002 |
| Samples + Tween 80 added Concentration of Tween 80: | | |
| 0.0001% | 60 | <0.0002 |
| 0.001% | 60 | 0.001 |
| 0.0025% | 30 | 0.002 |
| 0.01% | 20 | >0.0012 |
| 0.1% | 0 | >0.0012 |
| Vessel + Tween (0.1%) pretreatment and subsequent filling of samples | | |
| after 1 × rinsing with WFI | 5 | 0.0004 |
| after 2 × rinsing with WFI | 25 | <0.0002 |
| after 3 × rinsing with WFI | 28 | <0.0002 |

What is claimed is:

1. A process for reducing particle or floc formation during preparation of a protein solution consisting essentially of:

a. rinsing, at least once, a glass vessel with a detergent solution;

b. further rinsing, one to three times, said glass vessel with distilled water or another detergent-free solvent;

c. adding the protein solution to the glass vessel after step b; and d. heat treating the protein solution within the glass vessel, wherein said particle or floc formation is reduced by about 70% or more.

2. The process as claimed in claim 1, wherein the protein solution is an albumin solution or a solution of blood clotting factors.

3. The process as claimed in claim 1, wherein the heat treatment is pasteurization.

4. The process as claimed in claim 1, wherein the detergent solution is a nonionic detergent solution.

5. The process as claimed in claim 1, wherein the detergent concentration in the heat treated protein solution is <0.0002%.

6. A protein solution prepared as claimed in claim 1.

* * * * *